(12) United States Patent
Hazot et al.

(10) Patent No.: US 10,612,001 B2
(45) Date of Patent: Apr. 7, 2020

(54) CARTILAGE GEL FOR CARTILAGE REPAIR, COMPRISING CHITOSAN AND CHONDROCYTES

(71) Applicants: ADVANCED CHITOSAN SOLUTIONS BIOTECH, Villeurbanne (FR); CENTRE NATIONAL DE LA RECHERCHE SCIENTIFIQUE, Paris (FR); UNIVERSITE CLAUDE BERNARD LYON 1, Villeurbanne (FR)

(72) Inventors: Pascale Hazot, Villeurbanne (FR); Frédéric Mallein Gerin, Lyons (FR)

(73) Assignees: ADVANCED CHITOSAN SOLUTIONS BIOTECH, Villeurbanne (FR); CENTRE NATIONAL DE LA RECHERCHE SCIENTIFIQUE, Paris (FR); UNIVERSITE CLAUDE BERNARD LYON 1, Villeurbanne (FR)

( * ) Notice: Subject to any disclaimer, the term of this patent is extended or adjusted under 35 U.S.C. 154(b) by 73 days.

(21) Appl. No.: 15/532,020

(22) PCT Filed: Dec. 1, 2015

(86) PCT No.: PCT/FR2015/053271
§ 371 (c)(1),
(2) Date: May 31, 2017

(87) PCT Pub. No.: WO2016/087762
PCT Pub. Date: Jun. 9, 2016

(65) Prior Publication Data
US 2017/0306295 A1 Oct. 26, 2017

(30) Foreign Application Priority Data
Dec. 1, 2014 (FR) ..................... 14 61746

(51) Int. Cl.
| | |
|---|---|
| A61L 31/00 | (2006.01) |
| C12N 5/077 | (2010.01) |
| A61L 27/36 | (2006.01) |
| A61L 27/38 | (2006.01) |
| A61L 27/20 | (2006.01) |
| A61K 35/32 | (2015.01) |
| A61L 27/22 | (2006.01) |
| A61L 24/00 | (2006.01) |

(52) U.S. Cl.
CPC ............ *C12N 5/0655* (2013.01); *A61K 35/32* (2013.01); *A61L 27/20* (2013.01); *A61L 27/225* (2013.01); *A61L 27/3612* (2013.01); *A61L 27/3654* (2013.01); *A61L 27/3817* (2013.01); *A61L 27/3895* (2013.01); *A61L 24/00* (2013.01); *A61L 2430/06* (2013.01); *C12N 2533/56* (2013.01); *C12N 2533/90* (2013.01)

(58) Field of Classification Search
None
See application file for complete search history.

(56) References Cited

U.S. PATENT DOCUMENTS

| | | | |
|---|---|---|---|
| 7,524,514 B2 * | 4/2009 | Brekke | A61K 31/337 424/484 |
| 2004/0171151 A1 * | 9/2004 | Domard | A61L 27/20 435/395 |
| 2005/0074742 A1 | 4/2005 | Domard et al. | |

(Continued)

FOREIGN PATENT DOCUMENTS

| | | |
|---|---|---|
| WO | WO 99/47186 A1 | 9/1999 |
| WO | WO 02/078760 A1 | 10/2002 |

(Continued)

OTHER PUBLICATIONS

Cai et al., "Biodegradable chitosan scaffolds containing microspheres as carriers for controlled transforming growth factor-β, delivery for cartilage tissue engineering," Chinese Medical Journal, vol. 120, No. 3, 2007, pp. 197-203.

Claus et al., "Cartilage-Characteristic Matrix Reconstruction by Sequential Addition of Soluble Factors During Expansion of Human Articular Chondrocytes and Their Cultivation in Collagen Sponges," Tissue Engineering: Part C, vol. 18, No. 2, 2012 (published online Nov. 11, 2011), pp. 104-112.

Correia et al., "Chitosan scaffolds containing hyaluronic acid for cartilage tissue engineering," Tissue Engineering: Part C, vol. 17, No. 7, Jul. 2011 (published online Apr. 22, 2011), pp. 717-730.

(Continued)

*Primary Examiner* — Susan T Tran
(74) *Attorney, Agent, or Firm* — Birch, Stewart, Kolasch & Birch, LLP

(57) ABSTRACT

The present invention concerns a method for obtaining an implantable cartilage gel for tissue repair of hyaline cartilage, comprising particles of chitosan hydrogel and cells that are capable of forming hyaline cartilage, said method comprising a step for amplification of primary cells in a three-dimensional structure comprising particles of physical hydrogel of chitosan or a chitosan derivative, then a step for re-differentiation and induction of the synthesis of extracellular matrix by said amplified cells, in the same three-dimensional structure, wherein said cells are primary articular chondrocytes and/or mesenchymal stem cells differentiated into chondrocytes. The present invention also concerns the cartilage gel obtained thereby, and its various uses for cartilage repair following a traumatic lesion or an osteoarticular disease such as osteoarthritis. The invention also concerns a three-dimensional matrix comprising particles of physical hydrogel of chitosan or of chitosan derivative, optionally supplemented with an anionic molecule such as hyaluronic acid or a derivative of hyaluronic acid or a complex of hyaluronic acid.

Figure 1:
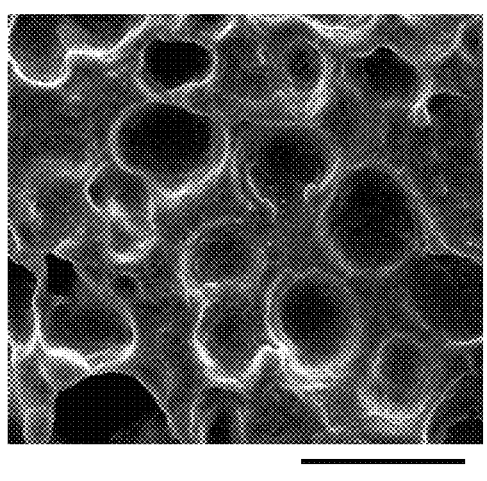

14 Claims, 5 Drawing Sheets
(5 of 5 Drawing Sheet(s) Filed in Color)

(56) References Cited

U.S. PATENT DOCUMENTS

| | | | |
|---|---|---|---|
| 2009/0022770 A1* | 1/2009 | Andersson | A61L 24/0036 424/423 |
| 2010/0178345 A1* | 7/2010 | Hung | A61K 9/5026 424/487 |
| 2013/0216592 A1 | 8/2013 | Delair et al. | |

FOREIGN PATENT DOCUMENTS

| | | |
|---|---|---|
| WO | WO 02/078761 A1 | 10/2002 |
| WO | WO 2011/104131 A1 | 9/2011 |
| WO | WO 2012/013895 A1 | 2/2012 |

OTHER PUBLICATIONS

Denuziere et al., "Chitosan-chondroitin sulfate and chitosan-hyaluronate polyelectrolyte complexes: biological properties," Biomaterials, vol. 19, No. 14, 1998, pp. 1275-1285.
Denuzière et al., "Interactions between chitosan and glycosaminoglycans (chondroitin sulfate and hyaluronic acid): physicochemical and biological studies," Annales Pharmaceutiques Françaises, vol. 58, 2000, pp. 47-53.
English translation of the Written Opinion of the International Searching Authority (Form PCT/ISA/237) issued in International Application No. PCT/FR2015/053271 dated Feb. 22, 2016.
Griffon et al., "Chitosan scaffolds: Interconnective pore size and cartilage engineering," Acta Biomaterialia, vol. 2, No. 3, May 2006, pp. 313-320.
Hao et al., "The support of matrix accumulation and the promotion of sheep articular cartilage defects repair in vivo by chitosan hydrogels," Osteoarthritis and Cartilage, vol. 18, No. 2, Feb. 2010, pp. 257-265.
Hautier et al., "Bone morphogenetic protein-2 stimulates chondrogenic expression in human nasal chondrocytes expanded in vitro," Growth Factors, vol. 26, No. 4, Aug. 2008, pp. 201-211.
Hoemann et al., "Tissue engineering of cartilage using an injectable and adhesive chitosan-based cell-delivery vehicle," Osteoarthritis and Cartilage, vol. 13, No. 4, 2005, pp. 318-329.
International Search Report (Form PCT/ISA/210) issued in International Application No. PCT/FR2015/053271 dated Feb. 22, 2016.
Iwasaki et al., "Chitosan-Based Hyaluronic Acid Hybrid Polymer Fibers as a Scaffold Biomaterial for Cartilage Tissue Engineering," Polymers, vol. 3, Dec. 27, 2010, pp. 100-113.

Lahiji et al., "Chitosan supports the expression of extracellular matrix proteins in human osteoblasts and chondrocytes," Journal of Biomedical Materials Research, vol. 51, No. 4, 2000, pp. 586-595.
Liu et al., "Optimal Combination of Soluble Factors for Tissue Engineering of Permanent Cartilage from Cultured Human Chondrocytes," Journal of Biological Chemistry, vol. 282, No. 28, Jul. 13, 2007 (previously published May 10, 2007), pp. 20407-20415.
Lu et al., "Effects of chitosan on rat knee cartilages," Biomaterials, vol. 20, 1999, pp. 1937-1944.
Montembault et al., "A material decoy of biological media based on chitosan physical hydrogels: application to cartilage tissue engineering," Biochimie, vol. 88, No. 5, May 2006 (available online Mar. 31, 2006), pp. 551-564.
Muzzarelli, "Chitins and chitosans for the repair of wounded skin, nerve, cartilage and bone," Carbohydrate Polymers, vol. 76, No. 2, 2009 (available online Nov. 13, 2008), pp. 167-182.
Nettles et al., "Potential Use of Chitosan as a Cell Scaffold Material for Cartilage Tissue Engineering," Tissue Engineering, vol. 8, No. 6, 2002, pp. 1009-1016 (14 pages total).
Park et al., "Injectable chitosan hyaluronic acid hydrogels for cartilage tissue engineering," Acta Biomaterialia, vol. 9, No. 1, Jan. 2013 (available online Aug. 27, 2012), pp. 4779-4786.
Subramanian et al., "Crosslinked chitosan: Its physical properties and the effects of matrix stiffness on chondrocyte cell morphology and proliferation," Journal of Biomedical Materials Research, vol. 75, No. 3, Dec. 2005 (published online Aug. 18, 2005), pp. 742-753.
Suh et al., "Application of chitosan-based polysaccharide biomaterials in cartilage tissue engineering: a review," Biomaterials, vol. 21, No. 24, 2000, pp. 2589-2598.
Tallheden et al., "Proliferation and differentiation potential of chondrocytes from osteoarthritic patients," Arthritis Research & Therapy, vol. 7, No. 3, Mar. 3, 2005, pp. R560-R568.
Tan et al., "Injectable In Situ Forming Biodegradable Chitosan-Hyaluronic acid Based Hydrogels for Cartilage Tissue Engineering," Biomaterials, vol. 30, No. 13, May 2009, pp. 2499-2506 (20 pages total).
Wang, "A novel hydrogel crosslinked hyaluronan with glycol chitosan," Journal of Materials Science: Materials in Medicine, vol. 17, 2006, pp. 1259-1265.
Yamane et al., "Feasibility of chitosan-based hyaluronic acid hybrid biomaterial for a novel scaffold in cartilage tissue engineering," Biomaterials, vol. 26, No. 6, Feb. 2005, pp. 611-619.

* cited by examiner 7A  7B

CARTILAGE GEL FOR CARTILAGE REPAIR, COMPRISING CHITOSAN AND CHONDROCYTES

The present invention relates to compositions, allowing inter alia the reconstruction of cartilage, and to a method for obtaining such compositions. More particularly, the present application relates to an environment or scaffold which is extremely favourable not only for the proliferation of cells that are capable of forming hyaline cartilage, but also for the synthesis of cartilage extracellular matrix by these cells; the cells in this environment or scaffold constitute an implantable composition which can be implanted to cartilage defects in humans or animals. The structure also constitutes a favourable environment during implantation.

Cartilage, or cartilaginous tissue, is constituted by specific cells, namely chondrocytes, distributed in an extracellular matrix, comprising at least 80% water. The chondrocytes are capable of synthesizing or degrading components of the cartilage extracellular matrix, composed of glycosaminoglycans and collagen fibers, essentially type II for hyaline cartilage. Thus, the chondrocytes are responsible not only for synthesis, but also for maintaining cartilaginous tissue.

Cartilage, and particularly articular cartilage in the adult, has a very poor self-repair capacity, primarily because of its avascular nature and because mature chondrocytes do not proliferate. Thus, cartilaginous lesions are essentially irreversible, and as a result constitute a major cause of pain and disability, in particular as a consequence of trauma, mechanical wear or a degenerative articular disease such as osteoarthritis. There are currently no entirely satisfactory therapeutic solutions that can be used to treat cartilaginous defects, and particularly large defects.

Various surgical procedures have been tested, consisting either of filling the lesion with materials intended to mimic the elastic and compressivity properties of natural cartilage, or implanting cells, in particular chondrocytes, with the aim that they will synthesize extracellular matrix de novo and thus repair the defect. A more promising approach is based on the implantation of cartilaginous tissue, i.e. a neo-tissue obtained from chondrocytes. Implantation of autologous chondrocytes ("ACI", autologous chondrocyte implantation) has now been used for several decades to treat patients suffering from cartilaginous defects. However, a major difficulty with chondrocytes implantation, and in particular autologous chondrocytes, resides in the number of cells to be implanted. In fact, in general, only a small number of chondrocytes can be removed from the native cartilage of the patient to be treated; as a consequence, it is necessary to carry out a first step of amplifying the chondrocytes removed in order to drastically increase their number. However, in vitro amplification of chondrocytes until a sufficient number of cells for implantation has proved to be very difficult. During this amplification step, it is in fact known that the chondrocytes dedifferentiate and lose their chondrocyte phenotype, then expressing type I collagen rather than type II collagen, such that when re-implanted, they do not lead to the formation of a tissue with satisfactory properties, but rather to a scar style tissue or, in the case of a cartilage repair, to the formation of a non-functional fibrocartilage, essentially composed of type I collagen. Some authors have proposed culture media which allow the chondrocytes which have dedifferentiated during the monolayer proliferation step to re-differentiate. However, those methods require relatively long periods, around 4 weeks, for the proliferation step (Liu et al., 2007) during which the chondrocytes have to undergo several passages in order to obtain a sufficient number. However, it has been shown that re-differentiation is more complicated after 2 passages in particular (Hautier et al., 2008).

Others have tested the re-differentiation of chondrocytes after the monolayer proliferation step, by seeding into 3D (three-dimensional) structures known as "scaffolds". Those structures offer the advantage of mimicking the architecture of cartilaginous tissue. Such an environment of is favourable to the re-differentiation of chondrocytes and to the synthesis of extracellular matrix, as evidenced by the secretion of proteoglycans and type II collagen (Tallheden et al., 2005). However, the prior multiplication step is deliberately shortened in order to limit the dedifferentiation of the chondrocytes.

Seeding into a 3D structure may also offer the advantage of facilitating in vivo implantation of chondrocytes, limiting cellular leaks and treating large defects.

Many materials have been tested for seeding chondrocytes into a 3D structure; alginate, collagen, polyethylene glycol and polylactic acid may be cited. The most appropriate are those which exhibit the following biological properties: cytocompatibility, low immunogenicity, and biodegradability, with non-toxic degradation products. Thus, natural polymers, which have these biological properties, certainly because of their chemical and biological similarities with living tissue, become the candidates of choice. Natural polymers are highly biocompatible, readily bioresorbable and bioassimilable by the organism.

A natural polymer which is often mentioned because of its attractive properties as a biomaterial for three-dimensional structures is chitosan.

In fact, according to the literature, this biopolymer is known to be biodegradable, biocompatible, non-toxic, haemocompatible, cytocompatible and, in addition, bioactive, haemostatic, healing, bacteriostatic and fungistatic.

In addition, chitosan is known to favour cellular adhesion. It is also known for its capacity to maintain the chondrocyte phenotype and stimulate the extracellular matrix synthesis process during the culture of chondrocytes. Furthermore, no infections or allergies have been reported which are related to chitosan. Thus, it is non-immunogenic. Regarding its resorption time, it is possible to vary it by modifying its physicochemical properties.

Chitosan is relatively easy to use and can be produced in various physical forms, in particular in solutions, films (Lahiji et al., 2000), fibers, sponges, beads, hydrogels or microparticles. For this reason, it has been used in an extremely wide variety of structures.

In the context of seeding chondrocytes into a 3D structure, a particular attention has been focused on structures that can provide both good distribution and maintain the chondrocytes, as well as an environment which is favourable to stimulation of their chondrogenic potential. With this objective, various approaches have been considered. Among the various structures tested, beads or fragments of material, polymers intended to encapsulate the cells, and hydrogels with a pore size which is adjusted so that the chondrocytes can be housed therein may be mentioned. Some authors have envisaged injectable compositions with a polymer encapsulating the chondrocytes (WO2011/104131, University of Liège et al). In accordance with some variations, the polymer is cross-linked in situ with the chondrocytes after injection on the defect (Hoemann et al, 2005). However, this approach suffers from the disadvantage that the injected chondrocytes have a tendency not to remain on the injection site because of the polymerization time. In contrast, other authors have tested some compositions, from a polymer cross-linked in situ, aiming at producing a tissue which can be grafted in the form of a plug (Hao et al, 2010). However, those methods can still cause difficulties during implantation.

In order to mimic the structure of cartilaginous tissue as best as possible, some authors have tested the hydrogel form, and more particularly physical hydrogel synthesized without adding any cross-linking agent and thus favouring biocompatibility and bioresorbability of the structure.

Thus, the production of a neo-tissue has been envisaged by bringing into contact with a physical hydrogel of chitosan (Montembault et al.). However, the prior multiplication step using monolayers is deliberately rapid in order to limit dedifferentiation of the chondrocytes before seeding, which means that multiplication of the cells is relatively low.

In a variation, the three-dimensional structure is largely resorbed during the in vitro step for synthesis of extracellular matrix, said structure no longer participating in the construct (see in particular WO02078760, Laboratoires Genevrier et al). Such a method is particularly lengthy to carry out, 4 to 6 weeks, before obtaining a neo-tissue that is capable of being 15 implanted, and said neo-tissue is no longer supported by the 3D structure at the time of the implantation.

Another polymer which has frequently been tested in the field of implantation of chondrocytes is hyaluronic acid. It is a natural polysaccharide which is also biocompatible and biodegradable. Furthermore, it is a major component of synovial fluid and glycosaminoglycans (GAG) present in articular cartilage. Hyaluronic acid aids in protecting the joints by increasing the viscosity of the synovial fluid and leading the cartilage more elastic. It has also been demonstrated that hyaluronic acid favours the expression of chondrocyte phenotype.

For this reason, hyaluronic acid has sometimes been combined with chitosan compositions in the culture of chondrocytes.

Some authors (Correia et al, 2011) have proposed, for example, three-dimensional sponge-like structures of a mixture of chitosan and hyaluronic acid for seeding chondrocytes. However, those structures cannot be used to obtain a homogeneous distribution of the cells; a cellular gradient is observed which increases from the exterior to the interior of the structure.

The document by Denuziere et al (1998) describes sponges of polyelectrolyte complexes in particular based on chitosan and hyaluronic acid. The polycationic chains of chitosan interact electrostatically with the polyanionic chains of the hyaluronic acid. The conclusion drawn, however, is that sponges of chitosan alone are preferred with respect to sponges of chitosan complexed with GAGs such as hyaluronic acid, for the proliferation of chondrocytes and for other associated biological properties.

A photocrosslinked hydrogel of chitosan and hyaluronic acid in which chondrocytes are encapsulated has also been proposed (Park et al., 2013). However, encapsulation of that type does not sufficiently favour proliferation despite relatively long culture times (proliferation rate 4 in 3 weeks).

Furthermore, according to the literature, although chitosan appears to have interesting properties for the reconstruction of cartilage, it should be noted that the degree of proliferation and synthesis of chondrocyte extracellular matrix on sponges of chitosan alone is highly dependent on the pore size of the structure (Griffon et al, 2006).

Some authors have even considered chitosan to be unsuitable to the proliferation of chondrocytes (Suh et al, 2000).

Currently, none of these 3D (three-dimensional) environments solves the problem of the proliferation of chondrocytes in a state compatible with the regeneration of cartilaginous tissue with the aim to be implanted. Thus, there is a major need to obtain, by using a rapid method, a satisfactory number of chondrocytes which are differentiated and capable of generating a cartilaginous tissue with suitable properties.

Furthermore, all of the methods propose modifications in the environment between the multiplication step and the differentiation step, which involves losses of material and time as well as the occurrence of trypsinization, which is damaging to the cells.

The present inventors have developed a method for obtaining chondrocytes in a sufficient number within a structure that can ensure both their perfect multiplication, their re-differentiation and the production of cartilaginous matrix. This structure is also suitable for implantation on the lesion.

In this context, the present inventors have found, in a completely unexpected manner that chitosan, in the form of particles of physical hydrogel is an excellent environment for chondrocytes, not only with a view to the synthesis of extracellular matrix of hyaline cartilage, but also with a view to their multiplication. In fact, against all expectations, the inventors were able to carry out, in the same chitosan structure, a proliferation step enabling a degree of proliferation to be obtained which is similar to, or even superior to that observed using the ordinary monolayer technique (on plastic or in sponges) and then readily allowing the re-differentiation of cells. As a consequence, the inventors have developed a method that can successfully be used to multiply chondrocytes directly after extracting in the primary state, then of inducing re-differentiation and synthesis of specific extracellular matrix in the same structure, thereby avoiding steps for trypsinization and structure modification. In addition, this structure is compatible with in vivo implantation without necessitating supplemental modification.

By means of the method of the invention, it is thus possible to obtain a composition comprising chondrocytes, distributed homogeneously within the structure and with a density that allows their re-implantation, in a time which is reduced compared with that which has been described until now, under very favourable conditions for the repair of cartilaginous tissues, in a structure directly compatible with implantation.

In the context of this description, the following terms have the following particular significance: The term chitosan means a polysaccharide composed of β-(1-4)-bound D-glucosamine units (deacetylated unit) and N-acetyl-D-glucosamine units (acetylated unit). It can be produced by chemical or enzymatic deacetylation of chitin; it also exists in the natural state. In chitosan of natural origin, the polysaccharide is generally associated with negligible quantities of beta-glucan. In the context of the present invention, the natural presence of beta-glucan in quantities in conformity with those found naturally in chitosan, is without influence. A chitosan is said to be "pure" even in the case of the presence of beta-glucan, as long as its presence is below 5% by weight with respect to the polysaccharide.

The term chitosan derivative means any chitosan polymer which has undergone a reaction aimed at modifying the chemical groups of the chitosan to change the functionalities, for example methylation, halogenation, etc. Preferably, a chitosan derivative does not have more than three types of modification, preferably only two types of modification, and more preferably only one type of modification. Chitosan derivatives which are particularly considered in the context of the present invention are glycol-chitosan, N-succinyl chitosan, and N- or O-carboxymethyl chitosan; this list is not limiting.

The degree of acetylation (DA) is the percentage of acetylated units with respect to the total number of units (acetylated and deacetylated units). It can be determined by Fourier transform infrared spectroscopy (FTIR) or by proton NMR.

The term chitosan hydrogel means that the constituent that is in the great majority, i.e. more than 80% or even more than 90%, or even 95%, of the hydrogel (by weight) is chitosan, apart from water. In similar manner, a chitosan derivative hydrogel means a hydrogel wherein the constituent that is in the great majority, i.e. more than 80%, or even more than 90% or 95% of the hydrogel, is the chitosan derivative, apart from water.

A "hydrogel of chitosan" or "of chitosan derivative" means a hydrogel preferably comprising at least 70% water, or even at least 80% water.

The term physical hydrogel means a hydrogel obtained by a method for gelling in an aqueous medium or in a hydroalcoholic medium not requiring the addition of a cross-linking agent.

The term chondrocyte phenotype means cells chondrocyte-like preferentially expressing type II collagen with respect to type I collagen.

The term hyaluronic acid means a polysaccharide composed of D-glucuronic acid and D,N-acetylglucosamine linked together via glycoside bonds.

The term hyaluronic acid derivative means any polymer of hyaluronic acid which has undergone a reaction aimed at modifying the chemical groups of the hyaluronic acid in order to change its functionalities, for example by esterification.

Thus, in a first aspect, the present invention concerns an in vitro method for obtaining a composition which is implantable by arthroscopy for cartilaginous repair, comprising particles or fragments of a physical hydrogel of chitosan or a chitosan derivative, and cells forming cartilage, preferably hyaline cartilage. The composition obtained by carrying out the method may be qualified as a cartilage gel. Such a cartilage gel in fact comprises cells synthesizing cartilaginous matrix, all distributed homogeneously, without a cellular gradient, in a three-dimensional structure based on particles of chitosan.

Such a method in accordance with the invention in particular comprises a step for amplification of primary cells in a three-dimensional structure (3D structure), then a step for re-differentiation and induction of the synthesis of extracellular matrix in this same three-dimensional structure, i.e. without changing the cells' environment.

As indicated above, chitosan is indeed a biocompatible, bioresorbable material which has non-toxic degradation products; it is non-immunogenic, cytocompatible and bioactive. It is also entirely compatible with pharmaceutical requirements as an implantable device. In the context of the invention, the hydrogel of chitosan or chitosan derivative is a physical hydrogel obtained without adding a cross-linking agent.

By means of this method, it is possible to obtain a composition or neo-tissue comprising chondrocytes within a matrix structure which is immediately ready for implantation, with undamaged chondrocytes which are capable of carrying out the synthesis of cartilaginous matrix after reimplantation. Because of the absence of a change of 3D structure, the method is easier to carry out and can be used to obtain a good quality neo-tissue. This method is also faster than those described in the prior art.

The method in accordance with the invention is thus characterized by the following steps:
(i) amplification of primary cells in a three-dimensional structure comprising particles of physical hydrogel of pure chitosan or chitosan derivative, then
(ii) induction of differentiation, or re-differentiation, and synthesis of extracellular matrix by said amplified cells within the three-dimensional structure of step (i).

These two steps are carried out in succession and not simultaneously, with the aim of optimizing the conditions and yields of each of these steps.

The Cells:

The cells which are amplified in the first step, are seeded into this 3D structure. They may be either chondrocytes or precursor cells of chondrocytes obtained from stem cells, for example mesenchymal stem cells, or induced pluripotent cells (IPS). They may be any cells differentiated into chondrocytes. Preferably, they are chondrocytes, and more preferably articular chondrocytes.

In the context of the invention, it is also possible to use co-cultures of differentiated chondrocytes and/or stem cells differentiated into chondrocytes.

The chondrocytes or stem cells may be obtained using any method known to the person skilled in the art, which can be used to recover cells from a biological sample which might contain them. Such methods have in particular been described in the document FR 2 965 278 (University of Caen Basse-Normandie, et al).

They are preferably human or animal cells, in particular equine or canine cells. They may be articular cells or auricular cells, or even obtained from the nasal septum.

Particularly preferred cells are human cells, for example human chondrocytes, and more particularly human articular chondrocytes for a human patient. This is also the case for an animal, in particular a horse or a dog.

The primary cells seeded into the structure may be allogenic, xenogenic, heterologous or autologous cells with respect to the organism which is to be treated. In accordance with a preferred implementation, they are autologous cells, i.e. they derive from the patient, human or animal to be treated. More preferably, they are therefore autologous human chondrocytes which could be re-implanted into the donor upon completion of the method in accordance with the invention. This is also the case for animal chondrocytes, for example for racehorses or dogs, which could also benefit from a chondrocytes implantation. It may also concern xenogenic or allogenic cells, because certain measures which are well known to those skilled in the art could be carried out to avoid rejection during implantation.

In accordance with one embodiment, they are not human embryo stem cells.

The Three-Dimensional Structure and Chitosan:

The cells are seeded into a three-dimensional structure or scaffold, or biomaterial, comprising fragments or particles of physical hydrogel of pure chitosan or chitosan derivative. Said particles then form a compatible scaffold or structure which is favourable to the formation of a three-dimensional tissue until the cells produce sufficient extracellular matrix to maintain the structure mechanically.

The cells are added after the phase for gelling and forming particles of chitosan hydrogel. The cells are thus located on the outside of the hydrogel fragments or particles; they remain on the surface of the fragments or particles and are neither imprisoned nor encapsulated in the hydrogel, nor do they penetrate into the pores of the hydrogel. Thus, they can move freely around the particles, as can nutrients and waste, during the various steps of the method of the invention. The mixture produced at the beginning of the culture between the chitosan particles and the cells mean that good distribution of the cells within the three-dimensional structure at the end of this method is favoured.

The chitosan used for the design of the three-dimensional structure or device is obtained by deacetylation of chitin, for example, which may derive from arthropods (shrimp, insects, crab, etc), from the endoskeleton of cephalopods (squid), or from the cell wall of fungi. Depending on its origin, chitosan may be in the α conformation (cell wall of fungi, shrimp, crabs) or in the β conformation (squid) or in the φ conformation (insects), which greatly influences its biological properties.

In the context of the present invention, the chitosan used may originate from these various sources, but a chitosan of non-animal origin will preferably be used for reasons of biocompatibility, low endotoxins content, reproducibility of batches and compliance with pharmaceutical standards. Preferably, the chitosan used in the context of the present invention is chitosan extracted from the cell wall of fungi, more particular the common mushroom, *Agaricus bisporus*. In fact, in the context of implantable devices, because of regulatory requirements, it is particularly advantageous not to have any material which is of animal origin. The chitosan used in the present invention, extracted from common mushroom, complies with pharmaceutical requirements in terms of the endotoxins content, microbiological residues and heavy metals.

Succession of Steps:

The method in accordance with the invention is characterized in particular by the succession of two steps, a first step for amplification of primary cells in a three-dimensional structure and a second step for induction of differentiation and synthesis of extracellular matrix (ECM) within the very same three-dimensional structure.

The major advantage of this method resides in the fact that it is not necessary to change the cells' scaffold between the amplification step and the re-differentiation step with synthesis of ECM, nor indeed between the re-differentiation step and that for implantation. This means that it is not necessary to carry out a cell trypsinization step at any time. In fact, after extraction, the primary cells are seeded into the structure of the invention, without a prior proliferation step, and thus without needing to detach them, in particular by trypsinization, or by any other means that is susceptible to damage the cell wall. They then proliferate within the structure, then are induced to re-differentiate and produce cartilaginous matrix, again without the need to detach them, to trypsinize them, or to make them undergo any other treatment of a nature that could damage the cell wall.

The method of the invention can thus be used to obtain cells which, after extraction, have not been damaged and have not been subjected to conditions of stress, which then can guarantee not only an optimization of the number of cells removed, by reducing cell mortality, but also guarantee that at the end of the method, the cells are not in cell death programmes and do not express signals which could be harmful to the host organism after reimplantation. At the end of one week of culture and in general, throughout the culture period, the cell viability is more than 90%, or even more than 93%, or even more than 97%.

Preferably, the two major steps of the method of the invention, i.e. amplification on the one hand then re-differentiation and ECM synthesis on the other hand, are distinct steps. The inventors have in fact observed that the capacity to proliferate and the capacity to produce ECM were preferably successive steps for cells such as chondrocytes, so that the proliferation yields and cartilaginous matrix synthesis yields were much better when the two steps were distinct. In addition, there are media which could favour one or the other of these steps, exclusively, such that it is preferable to carry them out one after the other. Preferably, the two steps as described are thus not only successive but also distinct, the second step only starting when the first step has been completed.

The amplification step is considered to be distinct from that for synthesis of the cartilaginous matrix when the number of chondrocytes increases during the first step and remains relatively stable during the second step with little or no amplification.

The amplification step is considered to be distinct from that for synthesis of the cartilaginous matrix as a function of the viscosity of the medium: a low viscosity is observed during the amplification step and an increased viscosity is observed during the second step, confirming the production of extracellular matrix.

Preferably, during the first step, synthesis of extracellular matrix is low.

It is also possible to observe whether such a matrix is synthesized by using immunohistochemical methods, for example, such as those described in the examples below.

Type II collagen (COLII) is a characteristic marker of hyaline cartilage; it is a homo-trimer with three α1 (II) chains, encoded by the gene Col2a1. The analysis of this type of collagen is conventionally carried out in order to identify differentiated chondrocytes.

Type I collagen(COLI), an $α1_2 α2_1$ heterotrimer produced from the genes Col1a1 and Col1a2, is conventionally considered to be a marker for the dedifferentiation of chondrocytes.

The method in accordance with the invention is characterized by maintaining the capacity of the cells which have been placed in culture within the structure to re-differentiate into chondrocytes. The term "maintain this capacity" means that the majority of the cells, at the end of the second step, have a chondrocyte phenotype, preferably at least 60%, preferably at least 70%.

The inventors have in fact observed that the majority of cells seeded into the structure as described, based on hydrogel particles of chitosan or a derivative thereof, have a stable chondrocyte phenotype during the second step of the method for the synthesis of extracellular matrix. At the end of the method, the cells in the composition have no or little expression of type I collagen and/or do not produce it on the protein level, but express a COLII/COLI differentiation index which is greater than 1. Preferably, the cells present in this composition synthesize the proteins of type II collagen with a COLII/COLI protein ratio greater than 1, preferably greater than 1.5; and/or the proportion of type II collagen messenger RNA is significantly higher than the proportion of type I messenger RNA.

The method in accordance with the invention as described above can preferably be used to obtain the cartilage composition or gel which is ready for implantation in less than 40 days, preferably less than 36 days, or even less than about thirty days, for example less than 28 days, or indeed less than 21 days. Thus, from a biopsy of chondrocytes or of primary stem cells differentiated into chondrocytes, it is possible to obtain a composition which is ready for implantation, having a sufficient number of chondrocytes to be able to repair the articular lesion, in one month and a half, or less than one month, or less than three weeks.

To this end, the amplification step is carried out in one to three weeks, preferably in approximately two weeks, 12 to 16 days, or even in less than two weeks.

During this step, the multiplication of the number of living cells with respect to the number of cells initially seeded into the structure is at least 4, or even at least 6, or even at least 7 or more than 7.

Clearly, it may be decided to prolong the multiplication step for a time sufficient to obtain a predetermined number of cells, preferably provided that confluence is not reached. The cell density during seeding into the 3D structure must clearly be adapted as a consequence.

In accordance with a preferred implementation, the multiplication step lasts between 1 and 3 weeks and must be able to multiply the cells inside the 3D structure by a ratio of at least 4, or even at least 6, or even at least 7.

As a consequence, a biopsy of 300 mg to 500 mg of cartilage comprising approximately $10^6$ to $1.5 \times 10^6$ cells can be used to obtain, at the end of the amplification step, $4 \times 10^6$ cells to $10.5 \times 10^6$ cells due to the amplification rate observed by the inventors, with this being accomplished in 1 to 3 weeks. Such a number of cells is considered to be appropriate for implantation of a chondrocyte construct.

The second step, linked to re-differentiation accompanying by synthesis of the extracellular matrix, may have a variable duration.

With a view to reimplantation of cartilage gel, it is, however, preferable for such a step to last between 2 and 4 weeks, preferably approximately three weeks, or in fact less. The duration of this second step may optionally be adjusted as a function of the selected reimplantation mode.

At the end of carrying out the method of the invention, therefore, a composition or cartilage gel is obtained comprising chondrocyte cells distributed in a freshly synthesized cartilaginous matrix and which are capable of continuing the synthesis of cartilaginous tissue within a 3D structure composed of particles of physical hydrogel of chitosan or a chitosan derivative in a manner such that said composition or cartilage gel can be directly implanted in a human being or an animal, in particular to fill a cartilaginous articular defect, for example as a result of traumatic and limited defects of articular cartilage, or defects of the early superficial osteoarthritis type, or deeper defects of the osteochondral type.

Thus, upon completion of the method, a kit or cartilage gel is obtained which is ready for injection or implantation in vivo into a human being or an animal. If the 3D structure comprising the particles of chitosan hydrogel or chitosan derivative hydrogel can be partially biodegraded during the method, it is preferably only very slightly, preferably less than 50% of the initial 3D structure based on particles of chitosan hydrogel, before seeding.

Depending on the duration of the steps of the method of the invention, in particular the ECM synthesis step, the composition of the invention or cartilage gel could also be envisaged as being injectable into a human being or an animal. In this respect, the duration of the second step for ECM synthesis will be reduced by a few days in order to ensure that the composition remains injectable.

In contrast, in particular when it is desirable to obtain an implant with a very specific form, the ECM synthesis step will be adjusted in order to obtain the desired consistency to then be able to adjust the form of the composition to that which is desired. It is also envisageable that the structure could be produced directly in a container having the desired form and of carrying out the various steps of the method in this container in a manner such that at the end of the step for synthesis of cartilaginous matrix, the cartilage gel has the shape induced by the container.

The composition as described above comprises hyaline cartilage synthesized by the cells during the second step of the method, hence it's being called a cartilage gel.

A major advantage of the present invention resides in the fact that the composition obtained at the end of the method can be implanted directly. It is in particular not necessary to move the cells from the 3D structure, and thus is not necessary to make them undergo any treatment. It is also not necessary to ensure that the structure disappears, nor to await its degradation. In contrast, in accordance with the method of the invention, the chitosan based structure is still present at the end of the ECM synthesis step and forms part of the composition or neo-tissue intended to be implanted. In fact, such a structure acts as a scaffold to maintain the cells in a suitable environment so that, after implantation, it enables ECM to carry on its synthesis, and thus to be perfectly filled into the lesion, for example an articular lesion. The chitosan structure thus does not act solely to favour the synthesis of ECM in vitro, but also, after reimplantation, to support the implanted cells; thus, it participates in the structure of the reimplanted neo-tissue.

The structure also ensures an optimized spatial distribution of seeded cells, and thus allows the synthesized ECM to be distributed harmoniously during the method of the invention and also after reimplantation.

The number of cells implanted in the structure of the invention can vary as a function of the size of the lesion which it is to be filled, and also as a function of the number of cells which it is planned to collect for the purposes of seeding. However, preferably, at least approximately $10^5$ primary cells are seeded, in particular at least approximately $6 \times 10^5$ primary cells, or at least $10^6$ primary cells, preferably human, canine or equine primary chondrocytes; at the end of the method of the invention, the final composition preferably comprises at least $3 \times 10^5$ chondrocytes, or at least $6 \times 10^6$ chondrocytes, or perhaps more. In order to obtain a composition which can be implanted directly into a cartilaginous lesion, $10^6$ to $1.5 \times 10^6$ cells are preferably seeded in order to obtain 4 to $10.5 \times 10^6$ cells upon completion of the amplification step.

In accordance with one implementation of the invention, the chondrocytes in the composition have a concentration of approximately at least $10^6$ cells/g, preferably approximately at least $6 \times 10^6$ cells/g of 3D structure at the time of the beginning of the culture.

Culture Media:

In accordance with a particularly preferred embodiment, two different culture media are used. One is for the first amplification step and the other is for the second step for induction of re-differentiation and synthesis of ECM; the passage from one to the other of the steps is therefore carried out by modifying the medium, the two media being distinct.

In particular, during the first step, a medium favouring the proliferation of cells is used without inducing ECM synthesis. The proliferation of cells is generally accompanied by a phenomenon of dedifferentiation; however, a medium is used which preserves their capacity to re-differentiate into chondrocytes at the end of the proliferation step.

The inventors have in fact evidenced that within a three-dimensional structure, it is preferable to carry out an intense amplification step without in any way, inducing the synthesis of ECM.

Indeed, the three-dimensional structures and chitosan were known before the invention for their capacity to favour the chondrocyte phenotype by limiting dedifferentiation during the extracellular matrix synthesis step. Completely unexpectedly, the inventors have shown that it was possible to amplify the chondrocytes without inducing massive synthesis of extracellular matrix in a three-dimensional structure based on a chitosan hydrogel or a derivative.

A particularly suitable medium for the proliferation step is a medium inducing amplification, in particular a medium comprising fibroblast growth factor (FGF-2), and also insulin, corresponding to the medium termed "FI", as illustrated in the experimental section (Claus et al., 2012). FGF-2 is preferably present in a concentration between 2 and 10 ng/mL, and insulin is present in a concentration between 2 and 10 µg/mL. However, other culture media which are well known to the person skilled in the art may also be used, in particular any of the culture media mostly used for this kind of cell, but in monolayers. Because of the three-dimensional structure and the chitosan, the cells seeded inside the structure of the invention mainly conserve their round morphology and their capacity to subsequently re-differentiate into chondrocytes.

For the culture medium of the second step, media to be employed are those conventionally used in order to favour the differentiation or re-differentiation of dedifferentiated chondrocytes and to allow the specific synthesis of ECM. Such media are well known to the person skilled in the art. A particularly preferred medium comprises BMP-2 (bone morphogenetic protein 2); preferably, the medium is that used in the experimental section, in particular composed of BMP-2 and insulin, and preferably also triiodothyronine T3 (Liu et al., 2007, Claus et al. 2012), corresponding to a medium called "BIT". The BMP-2 is preferably in a concentration in the range 100 to 500 ng/mL, with the insulin in a concentration between 2 and 10 µg/mL and the triiodothyronine, T3, in a concentration between 50 and 250 mM.

The BMP-2 will preferably be from the same species as the cells used, i.e. a human BMP-2 for human cells. This is also the case for animal cells.

As was the case for the culture medium of the first step, culture media are preferred for the second step, which do not oppose subsequent reimplantation of the composition at the end of the ECM synthesis step. This in particular prevents the compounds from running the risk of generating rejection reactions which are incompatible with the Regulation for implantable devices.

In addition, steps for eliminating the culture medium before injection or reimplantation at the end of the two steps mentioned above may be envisaged.

The first and the second step may independently be carried out under normoxic or hypoxic conditions.
Production of Chitosan Hydrogel:

The hydrogel of pure chitosan or chitosan derivative is produced from chitosan, preferably extracted from fungi and having a weight average molecular weight (Mw) which is preferably more than 150 kDa (i.e. 150 000 g/mol) in order to favour the physical gelling process by the presence of long macromolecular chains. It is preferably in the range 150 to 220 25 kDa.

If the chitosan has a substantially different molar mass, in particular if it is extracted from another source, the method for producing the physical hydrogel of chitosan, as described in the experimental section, could readily be adapted by the person skilled in the art using techniques which are well known.

In addition, it is also possible to use chitosan for the hydrogel which has a variable degree of acetylation; preferably, however, the acetylation degree of the chitosan is in the range 5% to 60%, preferably more than 25%, for example between 25% and 60%, or between 28% and 40%. This acetylation degree in effect induces an environment which is favourable to cells, leading to good adhesion between the hydrogel formed and the cells, and to good chondrogenesis results.

With a view to the formation of hydrogel, a solution of chitosan is preferably used wherein the concentration is sufficiently high to allow the macro molecular chains to become entangled and thus to favour physical gelling. In the context of the invention, the hydrogel is in fact obtained by an entirely physical process without using any chemical cross-linking agent. The concentration of chitosan in solution may be in the range 0.5-4% (w/w), preferably more than 1.5%, or even 2%. Preferably, the chitosan or the chitosan derivative has a concentration by weight in the hydrogel in the range 3.4% to 4.2%, before neutralization.

Several chitosan gelling methods may be used in the context of the present invention. The following particularly suitable methods may in particular be used, such as physical gelling with gas (ammonia) or physical gelling in a hydroalcoholic or aqueous medium.

Preferably, the hydrogel used in the context of the present invention is obtained by means of an evaporation method carried out in an alcoholic medium, as illustrated in Example 1 in the experimental section; such a method is also known as hydroalcoholic gelling.

The hydrogel obtained preferably has a thickness between 3 and 5 mm.

The pore size of the hydrogel obtained must be both smaller than the size of the cells and also sufficient to allow free diffusion of nutrients and elimination of waste. The embodiments described above and implemented in the experimental section can be used to obtain a pore size of this type. It should be noted that in the context of the present invention, the hydrogel of chitosan or chitosan derivative is such that the pore size cannot allow the penetration of cells into the interior of the hydrogel. The cells seeded into the three-dimensional structure in accordance with the invention thus proliferate without penetrating inside the hydrogel. Because the cells do not multiply in the pores of the hydrogel, and they can move freely around the hydrogel particles, this means that a homogeneous distribution of the cells inside the structure can be obtained without the substantial cellular gradients reported in Correia et al., 2011.

The person skilled in the art will be able to determine the pore size of a hydrogel and adjust the parameters for its production in order to ensure that the pore size is sufficiently small to prevent cells from penetrating, in particular chondrocytes, while nevertheless allowing the free diffusion of nutrients.

In order to obtain hydrogel particles constituting the base of the three-dimensional structure of the invention, the hydrogel obtained in this manner is manipulated using any suitable means well known to the person skilled in the art; this ensures that the hydrogel is fragmented into particles.

The hydrogel particles obtained in this manner are irregular in shape, but preferably have a relatively homogeneous size distribution, i.e. 50% of the particles have a size between −20% and +20% of the mean size. In accordance with a preferred implementation, the particles have a mean size in the range 10 µm to 1500 µm; preferably between 200 µm and 1200 µm (1.2 mm), and more preferably between 400 µm and 700 µm. The term "particle size" means the length of the edge if the particles are assimilated to rectangles, the length of the largest diameter if the particles are assimilated to ellipses. The particles are preferably formed as ellipses.

The inventors have demonstrated the best results for particles with a mean size over one hundred microns, in particular above 60 or in fact above 400 µm and less than 1.2 mm.

A certain variability in the particle sizes of the chitosan hydrogel particles appears to be favourable to the culture of chondrocytes.

In accordance with a preferred embodiment, the hydrogel is initially obtained by gelling using the hydroalcoholic route, then fragmented using any appropriate means.

Design of the Three-Dimensional Structure:

The three-dimensional structure in accordance with the invention thus comprises particles of physical hydrogel of chitosan or one of its derivatives, as detailed above, constituting a three-dimensional structure within which the cells are seeded or migrate naturally. In accordance with a preferred embodiment, the cells are mixed with the particles of hydrogel. The physical hydrogel of pure chitosan or of chitosan derivative is preferably solely constituted by chitosan or a derivative and water in an amount which is preferably at least 70%, preferably at least 80%. In particular, this hydrogel composition contains neither chemical cross-linking agent nor any other polymer, in particular polysaccharide or a derivative, apart from the β-glucan naturally associated with chitosan. The large percentage of water ensures that it is in fact a hydrogel of chitosan and not a sponge-like structure or other structure obtained by lyophilization of a chitosan solution. It should be noted that the large percentage of water in the hydrogel can mimic the natural environment of chondrocytes as best as possible, since the cartilaginous tissue comprises approximately 80% water.

In accordance with a particularly preferred embodiment, an anionic molecule is added to the hydrogel particles of chitosan or chitosan derivative in order to reinforce the mechanical and biological properties of the three-dimensional structure. This molecule does not form a part of the composition of the hydrogel, but is a constituent added after gelling the hydrogel of chitosan or chitosan derivative, and preferably after producing the hydrogel particles. The anionic molecule thus interacts only at the surface of the hydrogel particles in accordance with the invention, thereby favouring the formation of "hairy" chitosan particles by linear chains of this anionic molecule.

The anionic molecule associated with the surface of the chitosan particles is preferably in the form of a polymer, for example hyaluronic acid, or chondroitin sulphate. The chitosan chains have positive charges due to the amine groups in the protonated form, $NH_3^+$, and the chains of this anionic molecule interact via electrostatic bonds, thereby forming a stable complex in physiological medium (pH in the range 5 to 8, and especially in the range 6 to 7). The anionic molecule can thus be used to electrostatically cross-link the fragments or particles of hydrogel by interacting with the cationic chains of chitosan on the periphery of the particles, thereby reinforcing the mechanical properties of the three-dimensional structure or scaffold within which the cells are seeded.

It should be noted that the anionic molecule may be added to the three-dimensional structure before seeding with primary cells, and thus be present during the step for proliferation and ECM synthesis, and thus also during the subsequent implantation of the composition. In the context of the invention, seeding primary cells into a three-dimensional structure free from the anionic molecule and adding the latter again either during the first multiplication step or at the end of the first step when the second re-differentiation step is begun, or at the end of the second step for re-differentiation and ECM synthesis before implantation, may also be envisaged.

The anionic molecule will preferably be hyaluronic acid, one of the components of synovial fluid, known for its chondroprotective properties and favourable to chondrogenesis. Thus, the quantity of hyaluronic acid necessary to modify the viscoelastic characteristics of the three-dimensional structure is added. The electrostatic interactions occur between the amine groups in the protonated form, $NH_3^+$, of chitosan and the carboxyl groups of the hyaluronic acid.

A derivative of hyaluronic acid or a complex of hyaluronic acid may also be used. The relative proportion of the anionic molecule with respect to the chitosan hydrogel is preferably in the range 1% to 10%, preferably in the range 1% to 3%.

The hyaluronic acid may be from animal origin, for example by extraction from rooster comb, or from non-animal origin, obtained by bacterial fermentation. In the context of the present invention, the hyaluronic acid will most preferably be selected to be from bacterial origin. In fact, the hyaluronic acid obtained by bacterial fermentation is known for its better properties of biocompatibility, thereby avoiding allergies and rejection, reproducibility of batches and compliance with pharmaceutical standards. The hyaluronic acid used in the context of the present invention complies with pharmaceutical standards.

Its molecular mass by weight is preferably 50 kDa to 4 MDa, and is preferably selected to be more than 500 kDa, preferably between 500 kDa and 2 MDa, for example between 1 MDa and 2 MDa.

More particularly, preferably in the context of the present invention, the components of the three-dimensional structure, which are hydrogel particles of chitosan or chitosan derivatives, with or without the addition of chains of anionic compound, must be resorbable in vivo. In order to obtain such a property, it is important that none of the components of the three-dimensional structure oppose its resorbable nature.

Preferably, the association of hydrogel particles of chitosan or chitosan derivatives, with or without the chains of anionic compound, will be resorbed after several weeks once implanted, for example after at least two weeks, preferably at least 4 weeks. It is generally preferable for the resorption time not to exceed 6 months, preferably not to exceed 4 months. Depending on the type of application envisaged, the resorption time may be adjusted by the person skilled in the art.

It is important to note that the compositions in accordance with the present invention may be adapted in terms of form, diameter, concentration, and content depending on the various targeted applications. In particular, the three-dimensional structure formed of hydrogel particles of chitosan or chitosan derivative with or without the chains of anionic compound may be produced in a manner such that its shape corresponds to that of the lesion observed into which it will be reimplanted upon completion of the method in accordance with the invention.

However, no dehydration step is necessary nor desired prior to reimplantation.

As discussed above, the method may be used to obtain a cartilage gel or composition which is ready for implantation or injection in vivo, in particular for a human being or an animal such as a dog or a horse.

However, prior to implantation, the medium may be changed, or additional compounds may be added, in particular compounds which are soluble in the three-dimensional structure. As an example, adding pharmaceutical compounds such as anti-inflammatory agents, anaesthetics, analgesics, corticosteroids, vitamins, minerals, compounds aiming at reducing the immune response and/or compounds favouring grafting may be envisaged, including all or a part of these compounds or a combination of these compounds; this list is not limiting.

In accordance with a second aspect, the present invention concerns a three-dimensional structure formed by particles of physical hydrogel of chitosan or a derivative of chitosan and an anionic molecule associated with these particles. Such a matrix may advantageously be used to seed chondrocytes, causing them to proliferate then synthesize extracellular matrix, more particularly matrix characteristic of hyaline cartilage, in particular for use in accordance with the present invention, before being implanted or injected in the form of cartilage gel, in particular into an articular defect. As demonstrated in the context of the present invention, such a structure can in fact be used to ensure not only the proliferation of cells such as chondrocytes, but also to provide an environment which is particularly favourable to the synthesis of hyaline cartilage matrix. The invention also concerns an implantable or injectable composition comprising this three-dimensional structure and differentiated chondrocytes that are capable of synthesizing cartilaginous tissue. It should be noted that the composition or cartilage gel also comprises cartilaginous matrix synthesized by the chondrocytes contained in the composition.

The various elements mentioned with regard to the method of the invention, are as described for the first aspect of the invention, in particular the three-dimensional structure, the chitosan or its derivative, the hydrogel, the particles and the anionic molecule. The preferred implementations in the context of this first aspect are also preferred in the context of this second aspect. In particular, the chitosan is preferably a chitosan obtained from fungi, and more particularly extracted from the cell wall of the common mushroom, *Agaricus bisporus*. The particles have the specific sizes given above, namely between 10 µm and 1200 µm, preferably between 400 and 700 µm on average. Thus, the structure is preferably a 3D structure formed by particles of physical hydrogel of chitosan with a mean size in the range 400 µm to 700 µm, where said chitosan is extracted from the common mushroom.

Concerning the anionic molecule, as explained for the method of the invention, this is preferably a polymeric molecule and more preferably hyaluronic acid or a derivative of hyaluronic acid or a complex of hyaluronic acid, and more specifically hyaluronic acid derived from bacterial fermentation.

The differentiated chondrocytes present in the composition of the invention are articular chondrocytes, for example. More preferably, they are human or animal chondrocytes, in particular canine or equine. The chondrocytes are differentiated chondrocytes with a chondrocyte phenotype, in particular with a COLII/COLI differentiation index greater than 1. Preferably, the chondrocytes present inside this composition principally synthesize proteins of type II collagen with a COLII/COLI protein ratio greater than 1, preferably greater than 1.5; and/or the messenger RNA content of the type II collagen is significantly higher than the messenger RNA content of type 1 collagen, with a COLII/COLI transcriptional ratio for the cells higher than 1, for example more than 100, or more than 1000.

In accordance with one implementation of the invention, the relative proportion of chondrocytes inside the composition corresponds to a concentration in the range $10^6$ and $10^7$ cells/g of 3D hydrogel structure, when culture is begun.

The composition of the invention may also comprise other compounds or molecules and in particular extracellular matrix (ECM).

Preferably, a composition as described or cartilage gel is capable of being obtained by carrying out the method of the invention, in particular by culturing cells inside the three-dimensional structure, then proliferating them, followed by their re-differentiation accompanied by ECM synthesis.

It is also possible to envisage adding additional compounds, in particular soluble compounds, for example selected from anti-inflammatory agents, anaesthetics, analgesics, corticosteroids, vitamins, minerals, compounds aimed at reducing the immune response and/or at favouring grafting, all or a portion of these compounds or a combination of these compounds; this list is not limiting.

As described in the context of the method of the invention, the three-dimensional structure as described is advantageously resorbable, in particular bioresorbable in vivo. The properties of the hydrogel of chitosan or a derivative of chitosan will be selected as a function of the timescale desired for integral resorption of the three-dimensional structure, once the composition has been implanted. Preferably, the resorption time will be adapted such that such a resorption occurs concomitantly with the synthesis of the cartilaginous matrix by the chondrocytes present in the composition; preferably, the resorption time will be adjusted in a manner such that the cartilaginous matrix formed by the chondrocytes substitutes itself in its entirety into the three-dimensional structure of the hydrogel of chitosan or chitosan derivative.

In accordance with another aspect of the invention, the composition as obtained at the end of the method of the invention or as described in accordance with the second aspect of the invention is for therapeutic and/or surgical use, in particular for use as an implant or construct in the repair or reconstruction of cartilaginous tissue, or in the treatment of osteoarthritis, and more generally in the treatment of any disease characterized by a degradation or disappearance of cartilaginous tissue, in particular cartilaginous defect, for example following traumatic and limited defects of articular cartilage, or deeper defects of the osteochondral type. Such a composition for in vivo use is envisaged in particular for surgery, for rheumatology or as a vector for an active principle. The composition or cartilage gel can be implanted by arthroscopy.

A particular envisaged use is in chondrocytes implantation. Preferably, the chondrocytes present inside the composition to be implanted are autologous or allogenic cells, preferably human, canine or equine chondrocytes.

In accordance with a further aspect, the present invention also concerns a three-dimensional structure formed by particles or fragments of physical hydrogel of pure chitosan or a derivative of chitosan and its use for seeding cells in vitro, in particular for the purposes of proliferation and synthesis of extracellular matrix, in particular for carrying out the method in accordance with the first aspect of the present invention. The three-dimensional structure is that described above; this is also the case for the hydrogel of chitosan or a derivative of chitosan. This hydrogel is preferably extracted from the common mushroom as explained above, with a weight average molecular weight which is preferably in the range 150 to 220 kDa. The hydrogel particles preferably have a mean size in the range 200 µm to 1.2 mm, more preferably in the range 400 to 700 µm. An anionic molecule is preferably added to the hydrogel particles of the three-dimensional structure; it is preferably an anionic polymer, more particularly hyaluronic acid or a derivative of hyaluronic acid or a complex of hyaluronic acid, in particular obtained by bacterial fermentation.

All of the preferred implementations detailed above concerning the elements of the three-dimensional structure are also applicable to this aspect of the invention, and more particularly to the following characteristics: the hydrogel particles preferably have a size in the range 200 µm to 1.2 mm, preferably in the range 400 to 700 µm, and/or the chitosan has a weight average molecular weight which is preferably more than 50 kDa, preferably in the range 150 to 220 kDa, and/or the chitosan has a degree of acetylation in the range 5% to 60%, preferably in the range 28% to 40%, and/or the hyaluronic acid has a weight average molecular weight in the range 50 kDa to 4 MDa, preferably in the range 1 to 2 MDa.

The proportion of hyaluronic acid with respect to the chitosan hydrogel is preferably in the range 1% to 10%, preferably in the range 1% to 3%. As described above, this three-dimensional structure is advantageously used for seeding or culturing primary cells, in particular primary chondrocytes, or primary stem cells differentiated into chondrocytes, in particular mesenchymal stem cells. However, other kinds of cells may be cultured in this three-dimensional structure, in particular bone cells, fibroblasts, keratinocytes, or combinations of certain of these cells; this list is not limiting. The present inventors have in fact demonstrated that this three-dimensional structure provides a three-dimensional architecture which is particularly favourable to cells, whether they are in proliferation or multiplication phases or in phases for the synthesis of extracellular matrix. Further, as described above, this three-dimensional structure is biodegradable and bioresorbable, and may therefore be implanted in vivo, into humans or animals, once seeded by the cells.

In the context of the present invention, in vivo implantation of a three-dimensional structure in accordance with the invention, i.e. a three-dimensional structure comprising fragments or particles of physical hydrogel of chitosan or a chitosan derivative, electrostatically cross-linked by an anionic molecule, preferably a polymer, in particular hyaluronic acid or a hyaluronic acid derivative or a hyaluronic acid complex, said structure being free from cells such that the 3D structure is precisely colonized in vivo by the cells, may also be envisaged.

The three-dimensional structure as described in the context of the various aspects of this invention is preferably sterilized before being seeded.

FIGURES

The patent or application file contains at least one color drawing. Copies of this patent or patent application publication with color drawing will be provided by the USPTO upon request and payment of the necessary fee.

FIG. 1: scanning electron microscopy micrograph of a physical hydrogel of pure chitosan.

Figure 2:
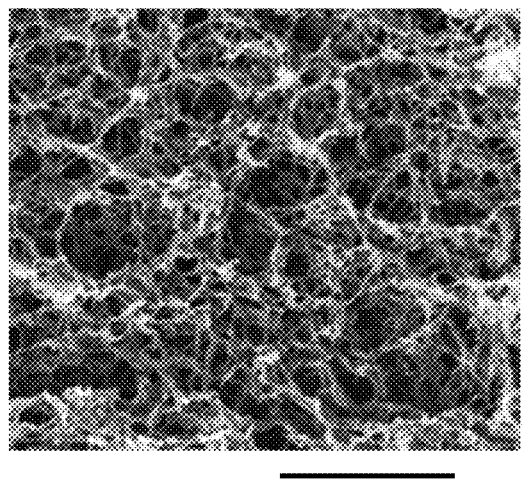
Figure 3:
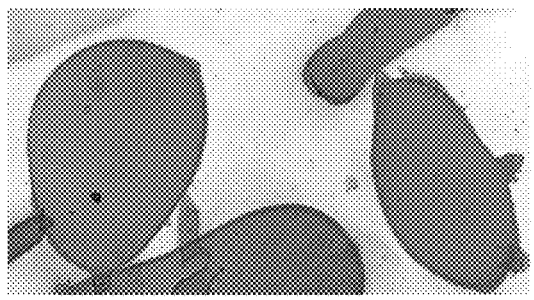

FIG. 2: scanning electron microscopy micrograph of a physical hydrogel of pure dehydrated chitosan FIG. 3: optical microscopy image of a physical hydrogel of pure chitosan after treatment with eosin.

Figure 4:
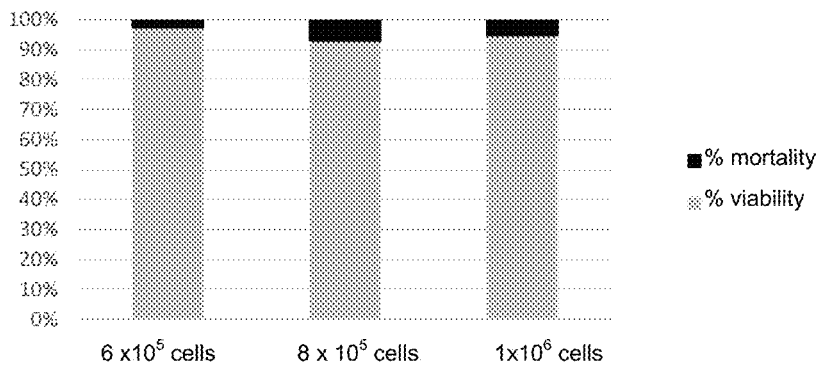

FIG. 4: shows the viability rates for cells seeded into a M1-type 3D structure as a function of the initial density of chondrocytes, measured with the Live and Dead kit on 7-day culture fractions (during amplification, in FI medium). The count of the dead cells (in black) and live cells (grey) was carried out with ImageJ software from fluorescence microscopic images with a magnification of ×20. The percentage of dead cells was calculated for each condition by calculating the dead cell/total cell ratio.

Figure 5:
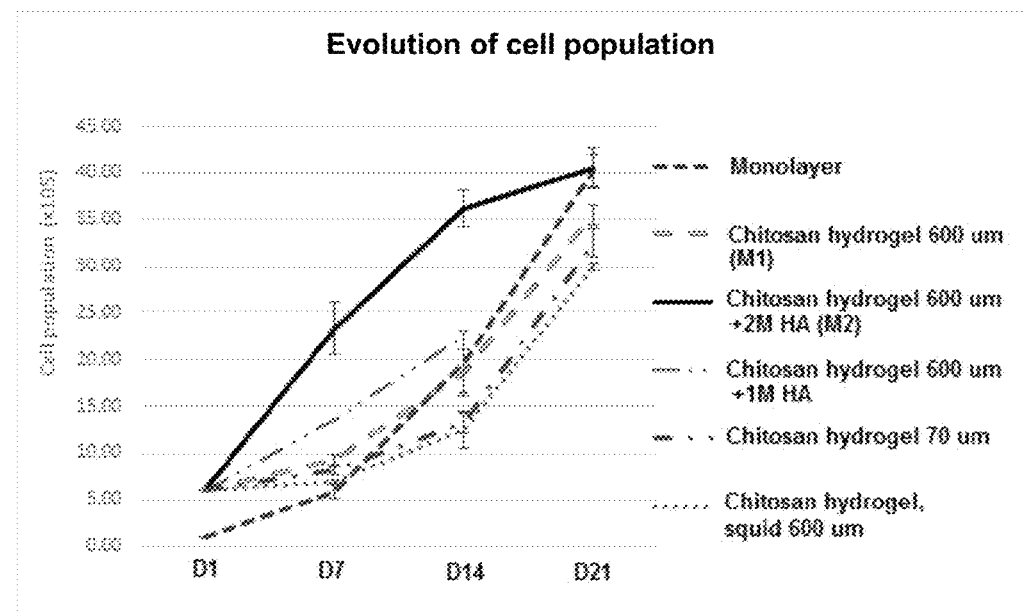

FIG. 5: shows the evolution as a function of time of the population of chondrocytes in 3D structures based on particles of physical hydrogel of chitosan extracted from fungi supplemented or not with hyaluronic acid, with different particle sizes or in 3D structures based on particles of physical hydrogel of chitosan extracted from squid, or also of chondrocytes cultured in monolayers under "FI" culture conditions. The number of cells is along the ordinate; the culture time in days is along the abscissa.

Figure 6:
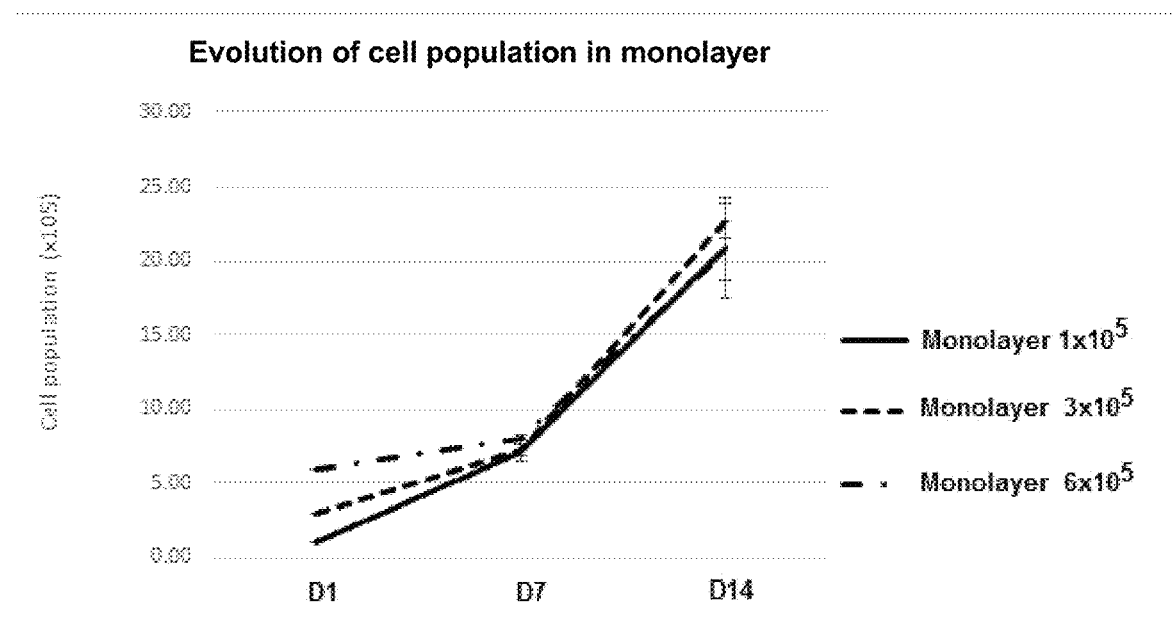

FIG. 6: shows the evolution in the population of chondrocytes as a function of time for different initial densities of chondrocytes cultured as monolayers, under "FI" culture conditions, confirming that the cell population obtained is identical beyond 7 days irrespective of the initial density.

Figure 7:
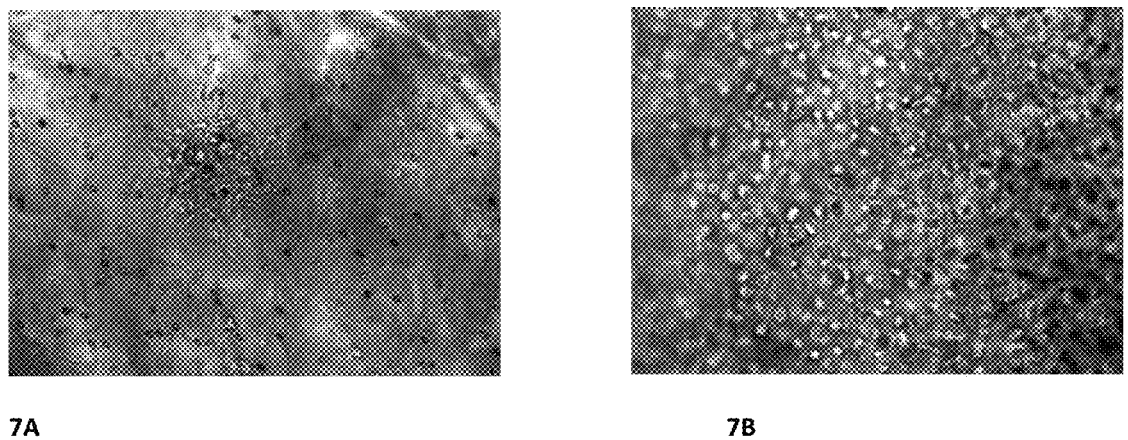

FIG. 7: optical microscopic images as a function of time of chondrocytes cultured inside the three-dimensional structures of pure hydrogel particles (M1).

FIG. 7A: represents cells obtained from the amplification step in FI medium 14 days after seeding.

FIG. 7B: represents cells during the ECM synthesis step in BIT medium 24 days after seeding, i.e. 10 days after inducing re-differentiation and ECM synthesis. The magnification ratio is ×20.

Figure 8:
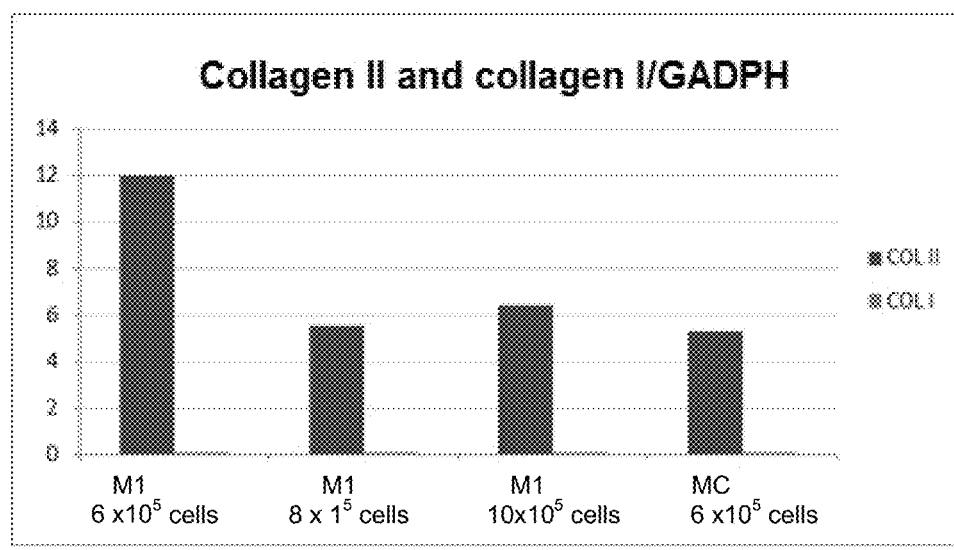

FIG. 8: shows the quantity of messenger RNA of type I collagen and type II collagen relative to the GAPDH gene, measured by quantitative RT-PCR for chondrocytes cultured in a 3D structure (M1) with several initial cell densities compared with the monolayer technique, after 35 days of culture.

Figure 9:
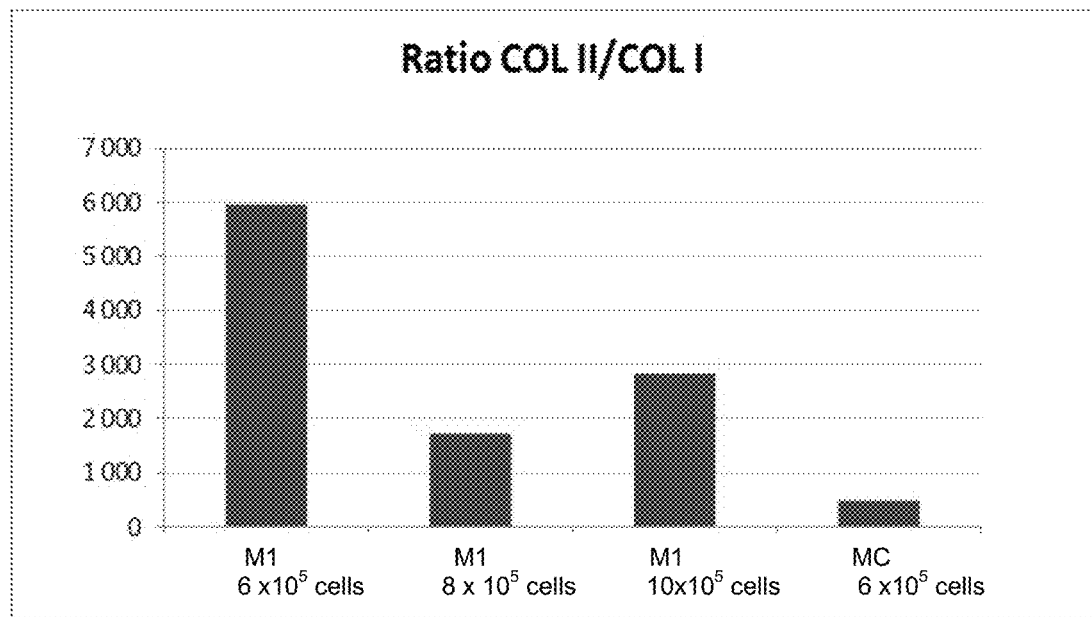

FIG. 9: shows the ratio of messenger RNA for the COLII/COLI genes obtained by quantitative RT-PCR, for chondrocytes seeded in a 3D structure (MD with several initial cell densities compared with the monolayer technique, after 35 days of culture.

Figure 10:
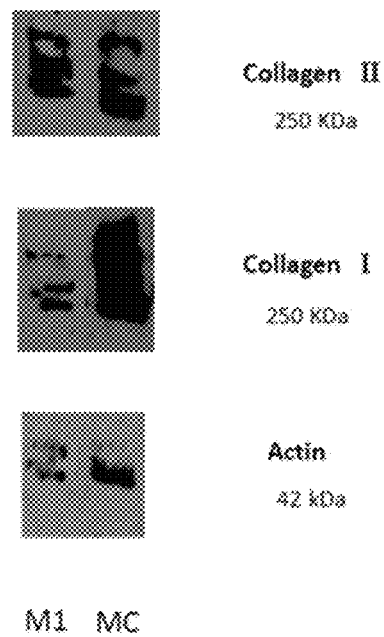

FIG. 10: shows Western blot analysis of the protein counts for type I and type II collagen, for chondrocytes cultured in a three-dimensional structure M1 compared with chondrocytes cultured in monolayers, after 35 days. The level of expression of actin acts as a control.

Figure 11:
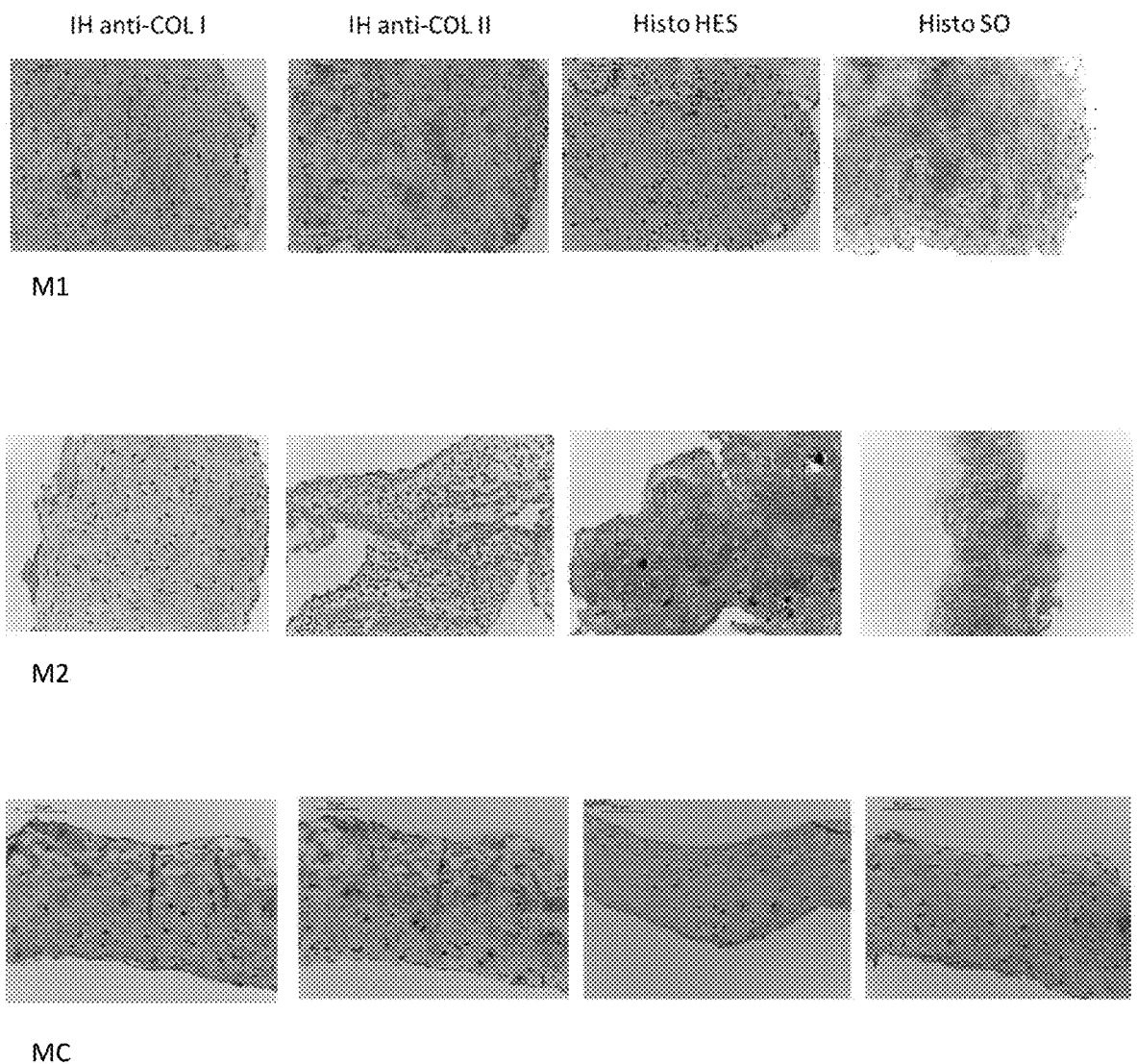

FIG. 11: shows the analysis, by immunohistochemistry, for chondrocytes cultured in 3D structure M1 and M2 compared with those cultured in monolayers (×20) (MC) after 35 days, for the same initial cell density ($6 \times 10^5$ cells) by HES and SO staining, as well as immunolabelling of type I collagen and of type II collagen.

EXAMPLES

Example 1: Synthesis of Physical Chitosan-Based Hydrogel

The chitosan used was from non-animal origin, extracted from the cell wall of the common mushroom, *Agaricus bisporus*. Its weight average molecular weight (Mw) was 170 g/mol; and its degree of acetylation (DA) was 32%. It was used in the form of a powder.

The pure chitosan was dissolved in an acidic solution of acetic acid (1% in water), in stoichiometric amounts with the amine groups of the chitosan. The solution was stirred at room temperature until the chitosan had completely dissolved, i.e. for at least 3 h, preferably at least 6 h.

Next, 1, 2 propanediol was added in a quantity identical to that of the acetic acid and stirring was continued for at least 30 min, preferably 1 h at room temperature. The mixture could then be degassed at room temperature, or under vacuum if necessary if the solution shows a lot of air bubbles.

The solution was then poured into containers like multi-well plates or 3 cm petri dishes, then it was left to stand, preferably overnight. The solution was then placed in a vacuum oven, preferably at 50° C., for the time necessary to allow a gel to form, preferably at least 20 hours.

The gelling step could also be carried out at room temperature, but then would have required longer times (5-8 days depending on the intrinsic characteristics of the chitosan).

The thickness of the solution before gelling could be in the range 2 to 7 mm, preferably in the range 3 to 6 mm, in order to favour evaporation and hydrophobic-like interactions for good gel setting.

The physical hydrogel obtained was then neutralized in a basic medium with a 0.1 N sodium hydroxide solution, preferably for 1 h. Next, several washes with water were carried out, preferably with sterile water. Each wash preferably lasted approximately 1 hour in order to 15 remove excess alcohol and bring the hydrogel to a neutral pH. In general, at least 6 washes were carried out.

The gel obtained thereby had a water content of approximately 80% by weight. The final concentration by weight of chitosan in the hydrogel was in the range 1% to 4.5% before neutralization, preferably between 3.4% and 4.2% before neutralization.

It is important to control the temperature and humidity conditions during the synthesis of the chitosan-based hydrogels, more particularly when it is extracted from fungi, preferably under room temperature conditions which are below 25° C.

The hydrogel obtained at the end of these various steps had a thickness of 3 to 6 mm, preferably between 4 and 5 mm thick, and was a translucent white colour and its surfaces were smooth and regular. However, its appearance could vary as a function of the intrinsic properties of the basic chitosan, in particular the degree of acetylation, the molar mass and the concentration. It was in the form of a viscoelastic block with mechanical properties which depended on the intrinsic characteristics of the starting chitosan, in particular and once again the degree of acetylation, the molar mass and the concentration.

The hydrogel obtained was easy to manipulate, detached without difficulty and without tearing the flat surface on which it had been produced.

Conventional scanning electron microscopic observation of the dehydrated hydrogel showed a fibrillar 3D structure, porous, similar to that of a living tissue, as can be seen in FIG. 2. Scanning electron cryomicroscopic observation of the hydrated hydrogel, as can be seen in FIG. 1, showed a pore size between 1-3 μm, which did not allow cells to penetrate inside the hydrogel but allowed free diffusion of nutrients and cellular waste.

Example 2: Synthesis of Particles/Fragments of Chitosan Hydrogel in Order to Produce the 3D Structure (Structure M1 and Structure M2)

Structure M1:

The chitosan hydrogel obtained at the end of Example 1 was cut into small squares with 1 mm sides then placed in 10 mL of water, preferably sterile water. The hydrogel was then ground with the aid of an Ultra Turrax, at 6000 to 17000 rpm for 10 seconds, carrying this out 2-4 times. In order to obtain particles with a homogeneous size and the expected diameter, grinding was preferably carried out at 6000 rpm for 10 seconds repeated 3 times, in order to obtain particle sizes of: 400-700 μm (50%), or in fact 250-900 μm (>80%), with a mean of the order of 650 microns.

The solution obtained was centrifuged, preferably at 1375 g for 7 minutes, in order to recover the pellet constituted by particles of chitosan hydrogel. FIG. 3 illustrates an example of the chitosan particles obtained. A mini-spoon was used to measure the quantity of particles of chitosan which would be brought into contact with the chondrogenic cells. Preliminary tests 25 validated the reproducibility of the measurement.

Structure M2:

In order to reinforce the viscoelastic properties of the 3D structure in which the chondrocytes 30 were seeded, the inventors also produced a second structure (M2) by adding an anionic constituent, interacting with the cationic functions of the chitosan. The selected polymer was hyaluronic acid, preferably from bacterial origin, since such a constituent is known for its better biocompatibility properties, in order to avoid allergies or any rejections. The molecular mass by weight of the hyaluronic acid used in producing the structure M2 was approximately 2 MDa. The hyaluronic acid was added after preparing the chitosan hydrogel particles.

Example 3: Culture of Cells in 3D Structure

The cells used in the context of this example were human chondrocytes obtained from human samples and treated in accordance with the protocol described in the document FR 2 965 278 (University of Caen Basse-Normandie, et al).

The hydrogel particles obtained at the end of Example 2, with hyaluronic acid (3D structure M2) or without hyaluronic acid (3D structure MD were sterilized, for example at 121° C. for 15 minutes, prior being brought into contact with the cells. Several mini-spoons of hydrogel particles were removed, preferably 2 mini-spoons corresponding to 80 to 84 particles, which were introduced into the wells of a 24-well culture plate which had been covered with an insert (pore size 8 μm). The cells were added thereto, between $10^5$ and $10^7$, preferably of the order of $6\times10^5$ cells/wells, per 80-84 particles of hydrogel, which were mixed carefully with the chitosan hydrogel particles. This proportion of cells with respect to the 3D structure corresponded to approximately $6.7\times10^6$ cells per gram of 3D structure at the moment of seeding.

Culture was carried out in a controlled atmosphere in an oven at 37° C., with a $CO_2$ percentage of 5% under normoxic conditions.

The cells adhered spontaneously to the chitosan hydrogel particles. The quantity of cells falling to the bottom of the well was considered to be negligible.

As a control, $6\times10^5$ cells obtained as described above were cultured in monolayers on plastic in 24-well plates under culture conditions which were identical to those described above for the 3D structures (controlled atmosphere in an oven at 37° C., with a $CO_2$ percentage of 5%, normoxia). The cells also adhered there spontaneously.

Example 4: Cell Proliferation Step

In this step, the selected culture medium was favourable to the multiplication of cells.

The selected medium was a 50/50 solution of DMEM-HAM F12+1% AB (streptomycin/penicillin)+10 FCS supplemented with "FI" solution comprising FGF-2 in a concentration of 5 ng/mL+insulin in a concentration of 5 μg/mL. (Claus et al; 2012).

After a short period, the mixture described in the preceding step was recovered from this culture medium which is known to favour the proliferation of cells.

During this amplification phase, the culture medium was renewed 3 times per week for the 10 cultures in the 3D structures, as was the case for the monolayer cultures. The proliferation period lasted between one and two weeks in order to obtain a sufficient number of cells.

The inventors observed that the amplification phase lasted approximately two weeks when the cells were seeded into a structure constituted by particles of pure hydrogel (3D structure M1) and could be shortened to 1 week in the presence of hydrogel particles supplemented by linear chains of an anionic molecule such as hyaluronic acid (3D structure M2).

Furthermore, the initial quantity of $6 \times 10^5$ cells/insert could of course be increased provided that the condition regarding number of cells/mass of hydrogel or number of cells/volume of hydrogel or number of cells/number of hydrogel particles is adhered to. By way of example, it is entirely possible to seed 1 to $1.5 \times 10^6$ cells/insert, provided that the necessary quantity of 3D structure is added in order to obtain more than $4 \times 10^6$ cells/insert at the end of the method, or even $10.5 \times 10^6$ cells/insert, or more.

Analysis by Optical Microscopy:

Analysis by phase contrast microscopy was carried out. It confirmed that the cells adhered well to the particles of chitosan hydrogel and that this environment was favourable to their culture. The culture conditions (three-dimensional structure M1 or M2, and FI culture medium) favoured the proliferation and division of the chondrocytes.

The cells observed could proliferate either in an isolated manner or in clusters/bunches. The cultures carried out in 3D structures of hydrogel particles exhibited mainly round cells. The elongated form, characteristic of fibroblasts, was not observed in the 3D structures M1 and M2, except occasionally at the periphery, i.e. at the interface between the structure and the external medium.

As a control, the inventors carried out monolayer cultures at the same time. After 24 hours of culture, in the same FI medium as the cells seeded into the structures M1 and M2, the chondrocytes adopted an elongated morphology characteristic of fibroblastic cells.

Viability of Cells:

The viability of the chondrocytes seeded inside the three-dimensional structures was measured with the Live and Dead kit on fractions of cultures at 7 days (during amplification, in FI medium). The dead cells (red) and live cells (green) were counted using ImageJ software from fluorescence microscope images, magnification ×20. The percentage of dead cells was estimated for each condition by calculating the dead cell/total cell ratio. The viability was more 15 than 93%, or in fact more than 97%, which demonstrated good compatibility with the 3D structure.

FIG. 4 illustrates the obtained results.

Proliferation Tests:

Proliferation tests were carried out by counting the total cells using the Cellometer T4 after detaching the cells with trypsin and staining the dead cells with trypan blue.

The measurements were carried out after 1 day (DI), 14 days (D14) and 21 days (D21) of culture after seeding the primary chondrocytes at D0.

FIG. 5 illustrates the evolution in the cellular population.

After 7 days, the increase in the number of cells was clearly observed. The cells survived and proliferated very well in the 3D structure as well as in monolayers (MC).

In the three-dimensional structures, M1 or M2, the cells remained round during the multiplication step, while they adopted an elongated shape like fibroblasts in monolayers.

Further, FIG. 6 illustrates that in monolayers, the cell population was identical from 7 days, irrespective of the initial density of the seeded cells.

In conclusion, at the end of this proliferation step, amplification of the cells in a three-dimensional structure composed of particles of pure chitosan hydrogel (structure M1) were observed to be almost as productive as in monolayers (MC), which is the reference protocol for the multiplication of cells such as chondrocytes, but it does involve a trypsinization step which can be avoided by using the structure M1.

Adding hyaluronic acid to the three-dimensional structure of chitosan hydrogel particles (structure M2) induced a very strong acceleration of cell proliferation, much greater than the M1 structure or the monolayer culture, in particular by a ratio of two.

Example 5: Differentiation and Production of Extracellular Matrix

In the context of the present invention, the steps for multiplication and differentiation were preferably distinct: firstly, the cells are multiplied and secondly, they are differentiated and produce extracellular matrix. The culture medium used for the preceding multiplication step was modified after 15 days. The culture medium "FI" was replaced by a medium "BIT" with the aim to favouring the step for differentiation of cells and the production of extracellular matrix.

Thus, the culture medium was preferably composed of: 50/50 DMEM-HAM F12+1% AB (streptomycin/penicillin)+10 FCS, to which a BIT solution composed of the following was added:

BMP-2, 200 ng/mL+insulin, 5 μg/mL+triiodothyronine, T3, 100 mM (Claus et al, 2012).

This fresh culture medium was renewed every two or three days. The period for re-differentiation and chondrogenesis preferably lasted 3 weeks. As a control, the same medium change was employed as for the cells cultured in monolayers.

Analysis by Optical Microscopy:

Cells with a fibrillar appearance in monolayers in FI medium are known to become round after 1 week of culture in BIT medium. The cells cultured in monolayers (corresponding to the control) changed appearance after changing to BIT medium, indicating that the change in culture medium indeed induced a change in the behaviour of the cells.

In the hydrogels (structures M1 and M2), the cells were primarily round at the end of the amplification phase and continued to be round during the entire phase for the production of extracellular matrix. This point is illustrated in particular in FIG. 7.

At the end of culture, D35, the cells were all round in the hydrogels (structures M1 and M2), less so in monolayers.

In the three-dimensional structures, the cells could agglutinate the particles of hydrogel and form a kind of "bead" with a compact form to a greater or lesser extent. This observation was made under the majority of conditions containing the hydrogels, but not in the monolayers, however, which acted as the control. This observation constitutes a proof of the strong production of extracellular matrix which had accumulated around the cells. The cells produced more extracellular matrix in a three-dimensional environment than in monolayers.

It should be noted that under certain conditions, however, the composition constituted by said beads remained injectable despite the synthesis of a large quantity of extracellular matrix. Whatever the case, the composition was implantable.

PCR Tests:

PCR was used to quantify the degree of transcription of the following proteins: COLI, COLII and GAPDH. The degree of transcription acts as a reference for comparing the levels of transcription of COLI and COLII. In fact, it is well known that the chondrocyte phenotype and the production of extracellular matrix are accompanied by a strong synthesis of COLII transcripts, while the COLI transcripts generally accompany the process of dedifferentiation, in particular into a fibroblast phenotype. The results are presented in FIG. 8.

The COLII/GAPDH results produced at the end of the ECM synthesis step, show that there are more COLII transcripts for the cultures in hydrogel than for the monolayer cultures. The COLI/GAPDH results show that, in contrast, there are more COLE transcripts in the monolayer cultures than in the cultures within the three-dimensional structures.

The result of the calculation of the COLII/COLI ratio is illustrated in FIG. 9. It shows that the ratio is indeed better, and in fact that re-differentiation is much better after dedifferentiation within the 3D structures constituted by particles of chitosan hydrogel compared with the monolayers.

The three-dimensional environment tested thus substantially favours the re-differentiation of dedifferentiated chondrocytes following prior intense multiplication, by a ratio of at least 6. This 3D structure favours the expression of chondrocyte phenotype.

The culture conditions (three-dimensional structure based on chitosan hydrogel, and BIT culture medium) thus favour the re-differentiation of chondrocytes and the production of cartilaginous matrix, compared with monolayer culture.

Western Blot Tests:

After having verified the degrees of transcription of the ColI and ColII genes as a function of the culture conditions (3D or monolayers), the degree of synthesis of the corresponding proteins was verified using the Western blot technique. The results of the various Western blots are illustrated in FIG. 10.

The results for the anti-COLII Western blot revealed the presence of COLII in all conditions. The results for the anti-COLI WB revealed more intense spots in monolayers. This observation corroborates the fact revealed in Q-PCR: the COLII/COLI ratio is higher in 3D hydrogel structures than in monolayers.

The Western blot analysis showed the expression of characteristic proteins of articular cartilage in the 3D structure.

Immunohistochemistry Results:

The compositions obtained were then observed using immunohistochemistry in order to compare the implementation of the novel method using the three-dimensional structure, and the traditional culture using monolayers, at the level of the synthesis of ECM, proteoglycans, and collagen types I and II. The results are illustrated in the photos of FIG. 11.

The presence of more proteoglycans in the three-dimensional structures (M1 and M2 in FIG. 11) than in the monolayers (MC in FIG. 11) are clearly observed because of the Safranin O staining (SO), which demonstrates the presence of GAG. Furthermore, the production of a lot of extracellular matrix and type II collagen was observed on the immunohistochemistry images for cells in the three-dimensional environment respectively evidenced with HES staining, which demonstrates the presence of nuclei and ECM, and by collagen II immunolabelling, which demonstrates the presence of COLII. Highlighting of the cells in the matrix by collagen I immunolabelling also confirms the quasi-absence of collagen I when the chondrocytes are cultured in the three-dimensional structures.

Example 6: Chondrocytes Implantation

The assembly of the cells and the 3D structure (i.e. either the structure M1 constituted by particles of chitosan hydrogel or the structure M2, constituted by particles of chitosan hydrogel supplemented with an anionic molecule like hyaluronic acid) constitutes, at the end of culture, i.e. between 3 and 6 weeks, a cartilaginous neo-tissue which may be injected or implanted by arthroscopy.

It is clearly possible to increase the number of cells in an insert by increasing the quantity of hydrogel, keeping however the same conditions for the number of cells with respect to the mass of hydrogel or the number of hydrogel particles constituting the 3D structure.

By way of example, for a sample of 0.3 g–0.5 g of human cartilage, $1–1.5 \times 10^6$ cells (chondrocytes) may be extracted. Since in the preceding examples the inventors have demonstrated that, starting from $6 \times 10^5$ initial cells per insert, it is possible to obtain from them $3.6 \times 10^6$ cells/insert in 0.09 g of hydrogel structure, corresponding to 80-84 particles of hydrogel, the following concentration data were obtained:

initial concentration of $6.7 \times 10^6$ cells/g of biomaterial, final concentration of more than $40 \times 10^6$ cells/g of biomaterial (3D structure).

For a sample from 1 to $1.5 \times 10^6$ cells, then, more than $3 \times 10^6$ cells can be obtained, or even more than $10.5 \times 10^6$ cells at the end of the method, after 2-5 weeks, which is amply sufficient for a construct where the recommended quantities are $3.2–6.5 \times 10^6$ cells.

In conclusion for the preceding examples, the following points are observed:

During the amplification/multiplication phase:
- an equivalent yield or in fact a greater yield in the three-dimensional structure comprising particles of pure chitosan hydrogel compared with monolayer culture,
- a much higher yield in three-dimensional structure comprising hydrogel particles supplemented with hyaluronic acid than in monolayers.

During the phase for differentiation and ECM production:
- a re-differentiation of cells inside 3D structures and in monolayers, as proved by the PCR, WB and immunohistochemistry analyses;
- a ratio of COLII/COLI messenger RNA which is significantly higher in the three-dimensional structure compared with monolayer culture,
- a COLII/COLI protein ratio which is significantly higher in three-dimensional structure than in monolayers,
- a stable chondrocyte phenotype in the 3D structure,
- abundant production of cartilaginous matrix in the 3D structure.

The succession of steps in the same three-dimensional medium comprising particles of chitosan hydrogel with/without structuring molecule, amplification then differentiation/chondrogenesis is highly favourable to the production of an injectable or implantable cartilaginous neo-tissue with excellent mechanical and biological properties.

The addition of hyaluronic acid improves the system by accelerating the process for the amplification of cells and meaning that the number of cells to be implanted can be increased, or a week can be saved over the overall protocol.

The configuration of the structure can be used to optimize the contact surface with the cells.

Example 7: Comparison Between Various 3D Structures

The inventors reproduced the 3D structures described in the preceding examples, in particular in Example 2, by varying the type of chitosan constituting the hydrogel particles, the size of the hydrogel particles and the presence and the concentration of hyaluronic acid. The proliferation ratios were compared and the results obtained are illustrated in Table 1. The value 1 was attributed to the structure M1 corresponding to particles of several hundred microns obtained from chitosan of fungi.

The proliferation ratio obtained with the structure M2 (extracted from fungi and supplemented with 2M hyaluronic acid) was twice as high as the structure M1 (extracted from fungi, not supplemented with hyaluronic acid), which itself makes it possible to obtain a proliferation rate 1.5 times higher than chitosan extracted from squid, or in fact with particles with a size of the order of tens of µm.

TABLE 1

Proliferation ratios

|  | Fragments, hundreds of µm | Fragments, tens of µm |
|---|---|---|
| Chitosan extracted from fungi supplemented with 2M HA | 2** |  |
| Chitosan extracted from fungi supplemented with 1M HA | 1.2 |  |
| Chitosan extracted from fungi | 1* | 0.67 |
| Chitosan extracted from squid | 0.67 |  |

*structure M1;
**structure M2

REFERENCES

Claus S, Mayer N, Aubert-Foucher E, Chajra H, Perrier-Groult E, Lafont J, Piperno M, Damour O, Mallein-Gerin F. Cartilage-characteristic matrix reconstruction by sequential addition of soluble factors during expansion of human articular chondrocytes and their cultivation in collagen sponges. *Tissue Eng Part C Methods.* 2012; 18(2):104-12.
Correia C R, et al. Chitosan scaffolds containing hyaluronic acid for cartilage tissue engineering. *Tissue Eng Part C Methods.* 2011 July; 17(7):717-30.
Denuziere A, Ferrier D, Damour O, Domard A. Chitosan-chondroitin sulfate and chitosan-hyaluronate polyelectrolyte complexes: biological properties. *Biomaterials.* 1998; 19(14):1275-85.
Griffon D J, Sedighi M R, Schaeffer D V, Eurell J A, Johnson A L. Chitosan scaffolds: interconnective pore size and cartilage engineering. *Acta Biomater* 2006 May; 2(3): 313-20.
Hao T, Wen N, Cao J K, Wang H B, Lü S H, Liu T, Lin Q X, Duan C M, Wang C Y. The support of matrix accumulation and the promotion of sheep articular cartilage defects repair in vivo by chitosan hydrogels. *Osteoarthritis Cartilage.* 2010 February; 18(2):257-65.
Hautier A, et al. Bone morphogenetic protein-2 stimulates chondrogenic expression in human nasal chondrocytes expanded in vitro. *Growth Factors.* 2008; 26(4):201-11.
Hoemann C D, Sun J, Legare A, McKee M D, Buschmann M D. Tissue engineering of cartilage using an injectable and adhesive chitosan-based cell-delivery vehicle. *Osteoarthritis Cartilage.* 2005; 13(4):318-29.
Lahiji A, Sohrabi A, Hungerford D S, Frondoza C G. Chitosan supports the expression of extracellular matrix proteins in human osteoblasts and chondrocytes. *J Biomed Mater Res.* 2000; 51(4):586-95.
Liu G, et al. Optimal combination of soluble factors for tissue engineering of permanent cartilage from cultured human chondrocytes. *J Biol Chem.* 2007 July; 13; 282 (28):20407-15.
Montembault A, Tahiri K, Korwin-Zmijowska C, Chevalier X, Corvol M T, Domard A. A material decoy of biological media based on chitosan physical hydrogels: application to cartilage tissue engineering. *Biochimie.* 2006 May; 88(5):551-64.
Park H, Choi B, Hu J, Lee M. Injectable chitosan hyaluronic acid hydrogels for cartilage tissue engineering. *Acta Biomater.* 2013 January; 9(1):4779-86.
Suh J K, Matthew H W. Application of chitosan-based polysaccharide biomaterials in cartilage tissue engineering: a review. *Biomaterials.* 2000; 21(24):2589-98.
Tallheden T, et al. Proliferation and differentiation potential of chondrocytes from osteoarthritic patients. *Arthritis Res Ther.* 2005; 7(3):R560-8.

The invention claimed is:
1. An implantable composition comprising a three-dimensional structure formed from particles of physical hydrogel of chitosan or chitosan derivative, associated with an anionic polymer at the surface of said particles, and differentiated chondrocytes or any cells differentiated into chondrocytes,
wherein said chondrocytes or cells do not penetrate into the particles of physical hydrogel,
and wherein the physical hydrogel of chitosan is synthesized without a cross-linking agent,
the chitosan has a weight average molecular weight of 150 kDa to 220 kDa, and
said anionic polymer is hyaluronic acid or hyaluronic acid derivative or a hyaluronic acid complex.
2. The implantable composition according to claim 1, wherein the chondrocytes synthesize type II collagen proteins and messenger RNA of type II collagen, expressing a COLII/COLI ratio higher than 1.
3. The implantable composition according to claim 1, obtainable by an in vitro method for obtaining an implantable composition for cartilage tissue repair comprising particles of chitosan hydrogel associated with an anionic polymer at the surface of said particles, and cells, said method comprising the following successive steps:
(i) amplification of primary cells in a three-dimensional structure comprising particles of physical hydrogel of chitosan or chitosan derivative, associated with an anionic polymer at the surface of said particles, then
(ii) induction of the synthesis of extracellular matrix by said amplified cells within the three-dimensional structure of step (i), in which said cells are primary articular chondrocytes and/or primary mesenchymal stem cells differentiated into chondrocytes and said cells are not human embryo stem cells, and in which said cells do not penetrate into the hydrogel particles.

4. The composition implantable by arthroscopy according to claim 1.

5. The implantable composition according to claim 1, wherein the water content in the chitosan hydrogel is more than 80%.

6. The implantable composition according to claim 1, wherein said particles of physical hydrogel of chitosan or chitosan derivative have a mean size in the range of 10 μm to 1.5 mm.

7. The implantable composition according to claim 1, wherein the chitosan is extracted from fungi.

8. The implantable composition according to claim 1, wherein the hyaluronic acid is extracted by bacterial fermentation, with a molecular mass by weight of more than 1 MDa.

9. The implantable composition according to claim 1, wherein the cell viability of said differentiated chondrocytes or said cells differentiated into chondrocytes, is more than 93%.

10. The implantable composition according to claim 1, wherein said cells are articular chondrocytes or are obtained from the nasal septum or atrial septum, and are of human, canine or equine origin.

11. The implantable composition according to claim 8, wherein said molecular mass by weight is more than 2 MDa.

12. The implantable composition according to claim 1, wherein the relative proportion of the anionic polymer with respect to the chitosan hydrogel is in the range of 1% to 10%.

13. The implantable composition according to claim 12, wherein the relative proportion of the anionic polymer with respect to the chitosan hydrogel is in the range of 1% to 3%.

14. The implantable composition according to claim 1, further comprising extracellular matrix (ECM) synthesized by said chondrocytes or cells within said three-dimensional structure.

* * * * *